United States Patent
Klaffenböck et al.

(10) Patent No.: US 11,000,269 B2
(45) Date of Patent: May 11, 2021

(54) MEDICAL INSTRUMENT

(71) Applicants: Johann Klaffenböck, Strobl (AT);
Lukas Klaffenböck, Strobl (AT);
Julian Mair, Munich (DE)

(72) Inventors: Johann Klaffenböck, Strobl (AT);
Lukas Klaffenböck, Strobl (AT);
Julian Mair, Munich (DE)

(*) Notice: Subject to any disclaimer, the term of this patent is extended or adjusted under 35 U.S.C. 154(b) by 315 days.

(21) Appl. No.: 15/776,330

(22) PCT Filed: Nov. 17, 2016

(86) PCT No.: PCT/AT2016/060111
§ 371 (c)(1),
(2) Date: Dec. 7, 2018

(87) PCT Pub. No.: WO2017/083897
PCT Pub. Date: May 26, 2017

(65) Prior Publication Data
US 2019/0083086 A1 Mar. 21, 2019

(30) Foreign Application Priority Data
Nov. 20, 2015 (AT) .............................. A 50991/2015

(51) Int. Cl.
A61B 17/04 (2006.01)
A61B 17/062 (2006.01)
A61B 17/06 (2006.01)
A61B 17/00 (2006.01)
A61B 17/29 (2006.01)

(52) U.S. Cl.
CPC ...... *A61B 17/0469* (2013.01); *A61B 17/0491* (2013.01); *A61B 17/06* (2013.01); *A61B 17/0625* (2013.01); *A61B 17/2909* (2013.01); *A61B 2017/00539* (2013.01); *A61B 2017/0472* (2013.01); *A61B 2017/0609* (2013.01); *A61B 2017/06047* (2013.01); *A61B 2017/2926* (2013.01); *A61B 2017/2936* (2013.01)

(58) Field of Classification Search
CPC . A61B 17/0469; A61B 17/0491; A61B 17/06; A61B 17/0625; A61B 2017/0472; A61B 2017/06047; A61B 2017/0609; A61B 2017/2936
See application file for complete search history.

(56) References Cited

U.S. PATENT DOCUMENTS

| 5,632,751 | A | 5/1997 | Piraka |
| 8,177,794 | B2 | 5/2012 | Cabrera et al. |
| 8,828,048 | B2 | 9/2014 | Klaffenboeck et al. |
| 8,968,339 | B2 | 3/2015 | Malkowski |
| 2013/0041388 | A1* | 2/2013 | Lane ............... A61B 17/062 606/145 |
| 2014/0257345 | A1 | 9/2014 | Holwerda |
| 2016/0053881 | A1 | 2/2016 | Zeller et al. |

* cited by examiner

Primary Examiner — Ashley L Fishback
(74) Attorney, Agent, or Firm — Dykema Gossett PLLC

(57) ABSTRACT

The invention relates to a device (100) for a medical instrument for applying a surgical suture, comprising a release unit (200) and an operating unit (300), said operating unit (300) comprising two pivotable gripper jaws (310, 320), each gripper jaw (310, 320) having a needle receptacle (340) and a needle fixation arrangement, said release unit (200) being configured to move the two gripper jaws (310, 320), and the trigger unit (200) also being configured to actuate said needle fixation arrangement.

10 Claims, 5 Drawing Sheets

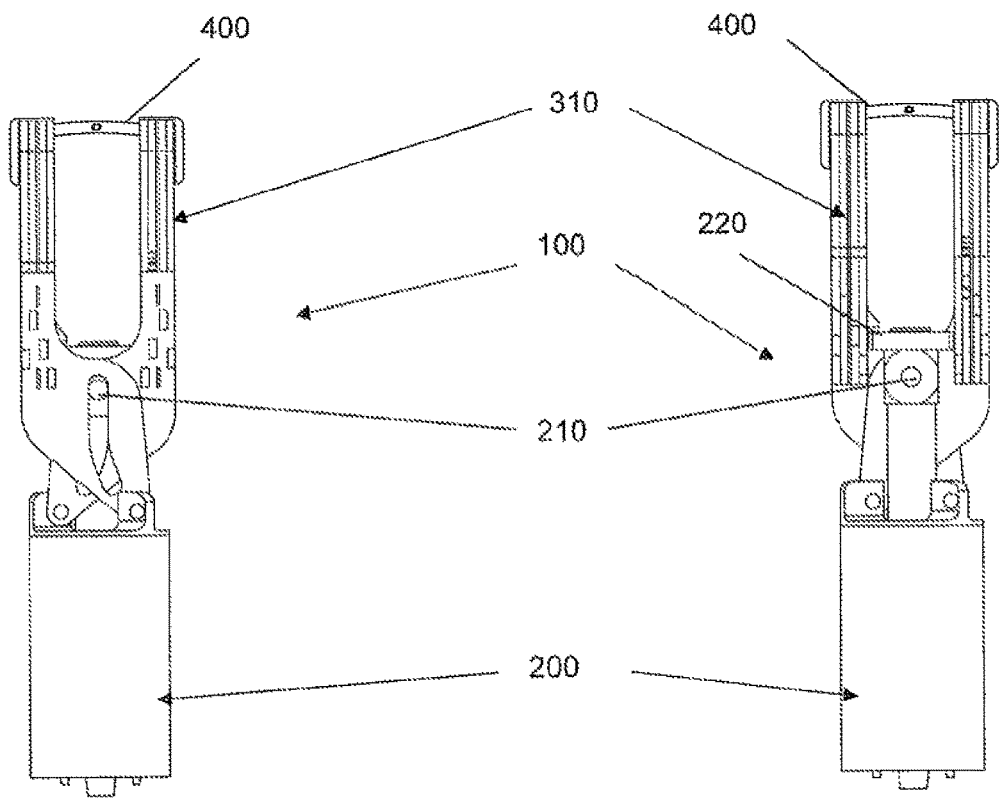
Figure 4A
Figure 4B
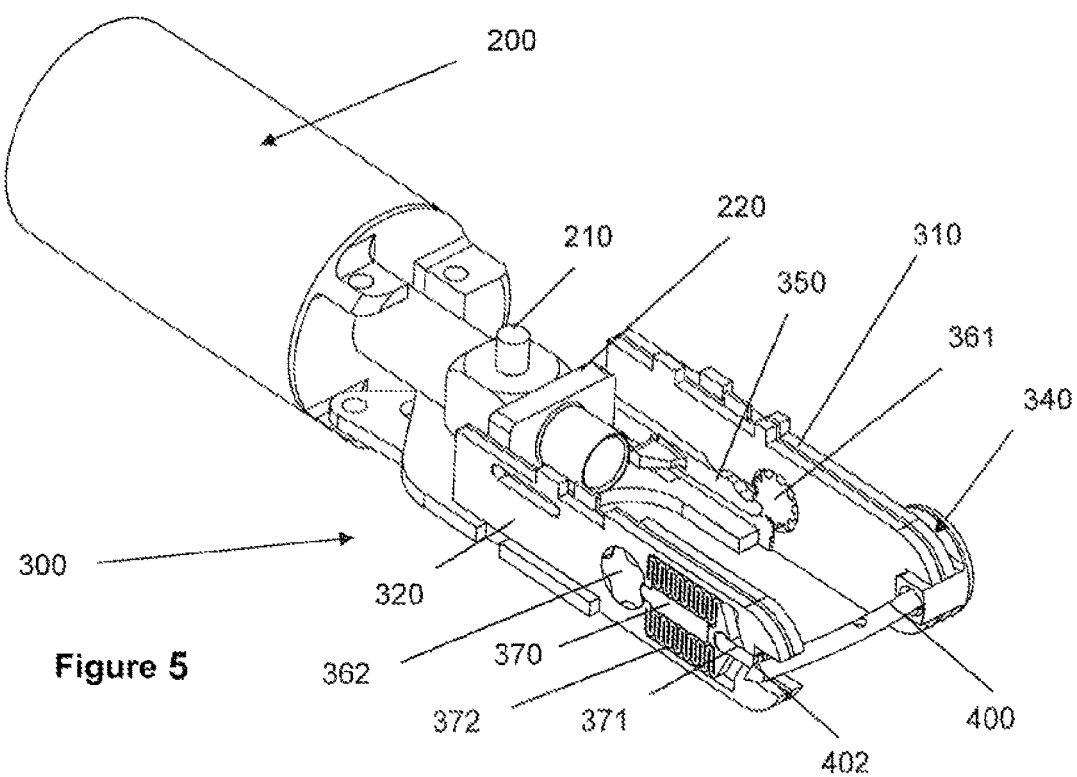
Figure 5

MEDICAL INSTRUMENT

The invention relates to a device for a medical instrument for applying a surgical suture, comprising a release unit and an operating unit, wherein the operating unit comprises two pivotable gripper jaws, each jaw having a needle receptacle and a needle-fixing device, and wherein the release unit is configured to move the gripper two jaws, wherein the needle-fixing device has at least one pawl element which is movable via the release unit, and the use of this device in a surgical instrument.

In many surgical procedures, it is necessary to apply a surgical suture. Due to new instruments, the surgical methods have improved so much that numerous procedures can be carried out endoscopically in order to be able to minimize the burden on the patient. Thus, EP 2 083 727 B1 describes a device of the type mentioned above, wherein a forceps-like end effector is configured to apply a surgical suture. Similar devices can also be found in EP 2 462 877 A2.

The devices for applying a surgical suture described in the prior art are often arranged in an extremely complicated manner and require two independent actuation systems, namely a first one for actuating the gripper jaws and a second one for fixing the needle in the respective gripper jaw or for the needle transfer between the two gripper jaws.

In U.S. Pat. No. 5,632,751 A, a surgical suturing device is disclosed, wherein two needle retainers are provided, each fixing either the needle tip or the needle end with the needle eye. The handling of this device during the applying of the suture is complicated, because it needs to be rotated before each needle stitch in its longitudinal axis about 180°. There is a risk that the suture material gets tangled in the device.

It is therefore an object of the invention to further develop the known devices, and in particular to provide a device which is easy to use and provides a stable and correctly set surgical suture.

This object is achieved by the device mentioned above according to the invention in that the at least one pawl element cooperates with a gear element, wherein the gear element has two gears, which are arranged substantially plane-parallel to each other and have a different number of teeth. The invention has the advantage that a single release system is responsible for both the movement of the jaws and the needle transfer. This allows easy operation and a slim design, which is particularly advantageous in endoscopic surgical methods.

In this context it should be noted that in the present disclosure "operating unit" is understood to mean that part of the device according to the invention which directly fulfills the stated task, namely the applying of a surgical suture, while the "release unit" controls the movements and functions of the operating unit.

According to the invention, it is provided that the release unit is additionally set up for actuating the needle-fixing device. In a general embodiment of the invention, this can be realized, for example, such that the release unit closes the gripper jaws in a first stroke, and fixes the needle in a gripper jaw in a second, subsequent stroke. It can be determined via an external signal in which of the two jaws the needle is fixed. This can be realized for example by an electrically controlled changeover member.

However, particularly preferred is a particular embodiment of the present invention, in which the switching occurs in a fully automatic manner. In this case, the release unit fixes, for example, the needle on a first gripper jaw in the second stroke of a first actuation, and in a subsequent second stroke of a second actuation, the needle on the second gripper jaw. After the first actuation takes place, an intermediate step is carried out in which the two gripper jaws are moved apart before the second operation takes place for fixing the needle in the second jaw, i.e. the needle transfer.

Preferably, the gripper jaws are hinged together and can be pivoted to each other during the operation or moved apart. This articulated connection is realized in a particularly preferred embodiment such that the two gripper jaws each have a slot-like recess with a first end and a second end, in which a release element of the release unit is arranged, preferably a sliding block slide. When a movement is triggered via the release unit, the pivoting of the jaws is caused. In this case, the sliding block slide is moved within the slot-like recess, wherein the curved course of the slot-like recess allows the adoption of defined operating conditions, which will be described in detail below.

A particularly simple and safe operation of the device according to the invention is made possible when the release unit has a hydraulic system. A hydraulic system suitable for this purpose can be found, for example, in EP 2 429 377 B1 of the applicant.

A precise transfer and fixation of the needle in the respective gripper jaw is obtained when the needle-fixing device has at least one pawl element which is movable via the release unit. In this case, the at least one pawl element interacts with a gear element.

The terms "gear" and "gear element" are not limited to machine elements that mesh with other gears or racks. According to the invention, a first gear cooperates with a pawl, which drives the gear by a movement in its longitudinal direction with appropriate operation. The second gear corresponds approximately to a wheel with a plurality of circumferentially disposed cams that move a push rod in its axial direction. It is provided in a particularly preferred way in this case that the second gear has twice as many teeth as the first gear.

In this case, the gear element has two gears, which are arranged plane-parallel to each other and have a different number of teeth. These two gears are interconnected so that as soon as a first gear is rotated, the second gear is also rotated. Particularly preferably, it is provided that the gear element is made in one piece.

Upon displacement of the pawl element along the gripper jaw the first gear of the gear element is rotated. Since the two gears of the gear element are connected to each other, the second gear element also rotates upon movement of the pawl element. Due to the different numbers of teeth of the two gears, a change in the actuation frequency is obtained, whereby different positions of the gripper jaws to each other and/or the at least one suture needle are adjustable.

It is further preferably provided that the needle-fixing device has at least one movable slide element, wherein the at least one slide element is adapted to fix at least one suture needle in the needle receptacle. In this case, the at least one slide element cooperates with the at least one gear element, in particular with the second gear, while, as already described above, the pawl element is in engagement with the first gear.

The movement of the slide element for fixing the at least one surgical suture needle and in particular the release of the fixation of the at least one surgical suture needle is supported in a further embodiment of the invention in that at least one first spring element cooperates with the at least one slide element.

Alternatively, in principle, a forced operation is possible in which the movement of the slide element in both directions is forcibly effected by the second gear. In this case, the sliding element engages around the gear, for example, and no spring element is needed.

A further improvement of the fixation of the at least one suture needle is achieved if at least one further spring element cooperates with the at least one pawl element.

The device according to the invention has proved to be particularly useful when used in a surgical instrument, in particular a flexible endoscopic instrument, which is preferably configured for transoral placement in a stomach. In this case, an actuating device is arranged at the proximal end of the elongated element of the surgical instrument for applying a surgical suture, wherein the device according to the invention is arranged at the distal end of the elongated element and interacts with the actuating device.

The invention is explained in more detail below with reference to non-limiting exemplary embodiments with associated figures, wherein:

FIGS. 4A and 4B show two side views of the device of FIGS. 1A and 1B in a third closed position;

FIG. 5 shows a first embodiment of the device according to the invention in a perspective view;

Figure 1A:
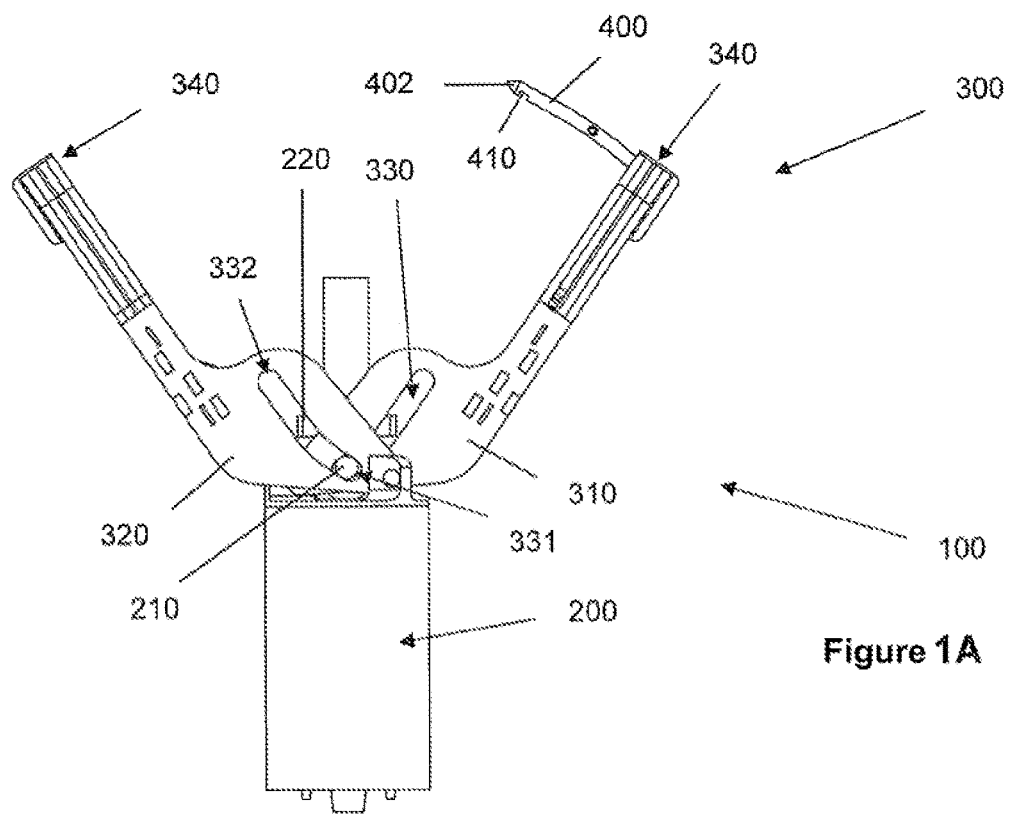
FIGS. 1A and 1B show two side views of the device according to the invention in a first, opened position.
Figure 1B:
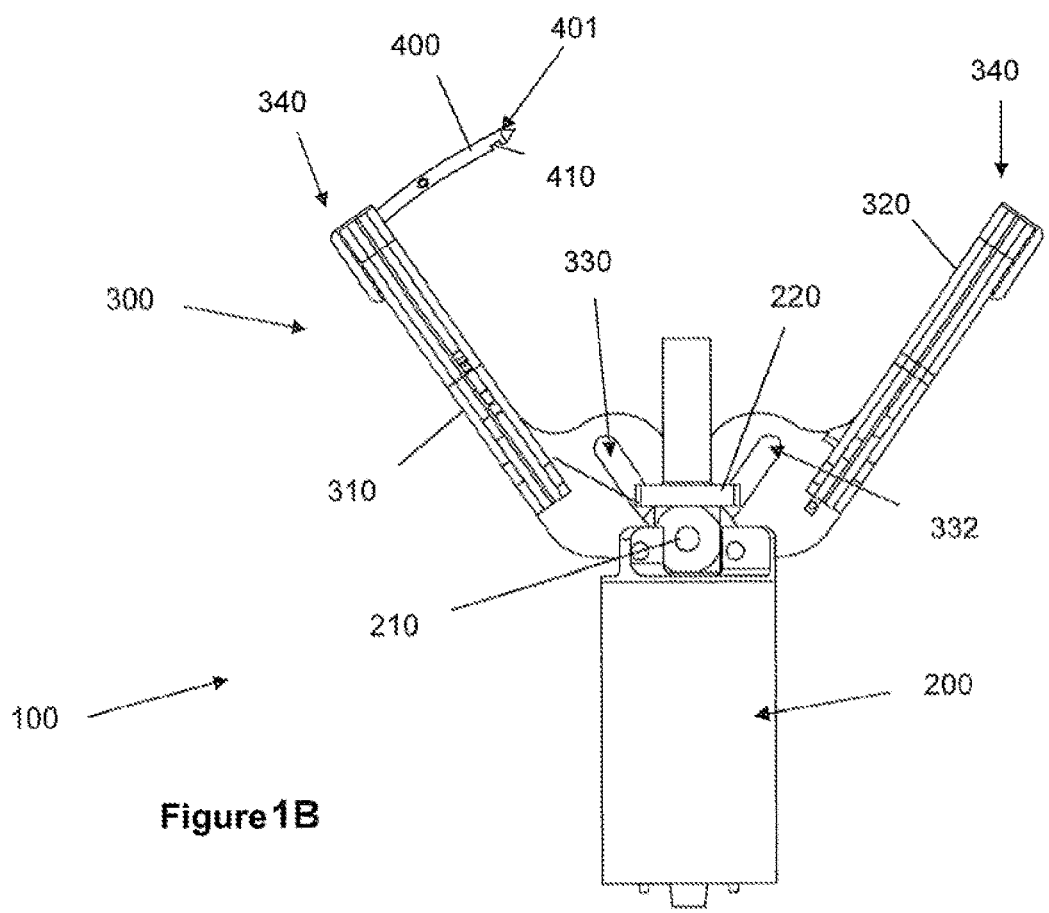

In FIGS. 1A and 1B, the device 100 according to the invention is shown in a first open position. This device 100 is usually referred to as an end effector, wherein in the context of this disclosure the term "end effector" is used synonymously for the device according to the invention for applying a surgical suture.

The end effector 100 has a release unit 200 and an operating unit 300. The release unit 200 is preferably designed as a hydraulic plunger system (not shown).

The operating unit 300, which is responsible for applying the surgical suture, has two gripper jaws 310, 320, which in this embodiment of the invention have a substantially mirror-image construction. The operating unit 300 is operated by the release unit 200, which relates both to the movement of the two gripper jaws 310, 320 and the fixing of the suture needle 400 in the gripper jaw 310, 320. The release unit 200 itself is in turn driven by an actuating element of a surgical instrument (not shown). For illustrative purposes, the outer housing of end effector 100 mounted in use is removed.

The gripper jaws 310, 320 each have a slot-like recess 330, wherein the gripper jaws 310, 320 are arranged to each other such that in the recesses 330, a sliding block slide 210 of the release unit 220 engages. In the open state of the end effector 100 shown in FIGS. 1A and 1B, the sliding block slide 210 is located at a first end 331 of the recess 330. The release unit 200 further has a stop plate 220 (FIG. 1B) which is in frictional connection with the sliding block slide 210. In this position, a suture needle 400 is fixed with its first end 401 in the needle receptacle 340 of the first gripper jaw 310. For this purpose, the suture needle 400 has a groove-like needle recess 410, which serves to fix the suture needle 400 in a needle receptacle 340.

Upon actuation of the sliding block slide 210, said slide moves in the recess 330 from the first end 331 in the direction of the second end 332. Upon actuation of the release unit 200, the sliding block slide 210 is moved to a second position, whereby the two gripper jaws 310, 320 are moved to each other, and the second needle end 402 of the suture needle 400 is inserted into the needle receptacle 340 of the second jaw 320 (FIGS. 2A and 2B).

If the sliding block slide 210 is moved further in the direction of the second end 332 of the slot-like recess 330 via the release unit 200, as shown in particular in FIGS. 3A and 3B and FIGS. 4A and 4B, the position of the gripper jaws 310, 320 no longer changes to one another. The movement of the sliding block slide 210 beyond the position shown in FIGS. 2A and 2B now causes a release of the two needle-fixing units, which are each arranged within the gripper jaws 310, 320 and are described in more detail below in particular in FIGS. 5 to 9.

Figures 2A, 2B:
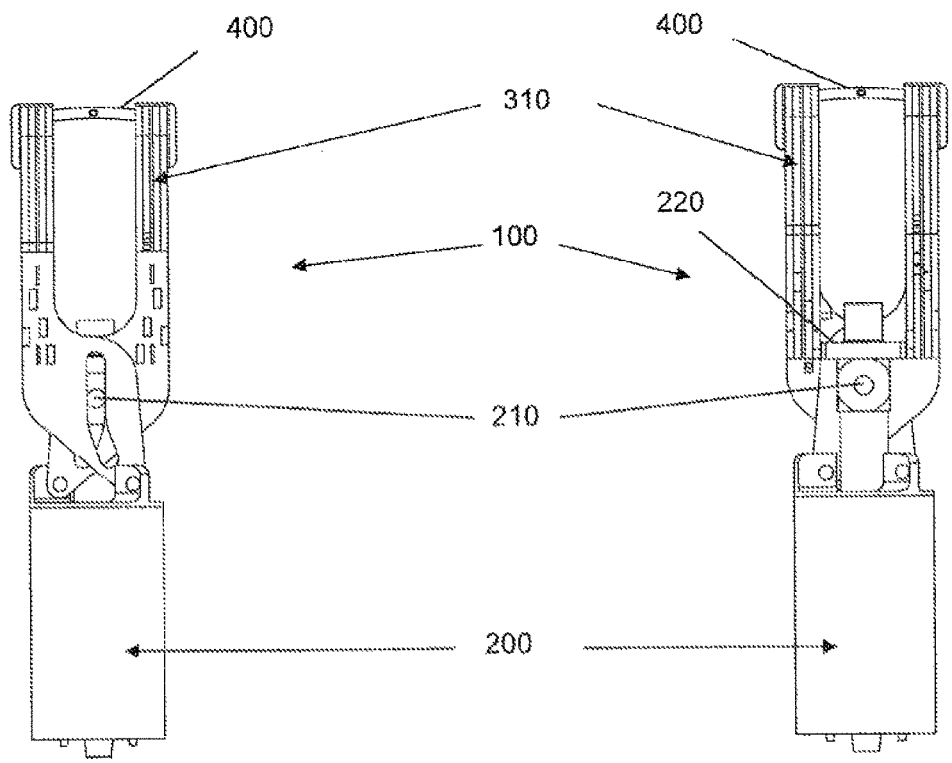
FIGS. 2A and 2B show two side views of the device of FIGS. 1A and 1B in a first closed position.
Figures 3A, 3B:
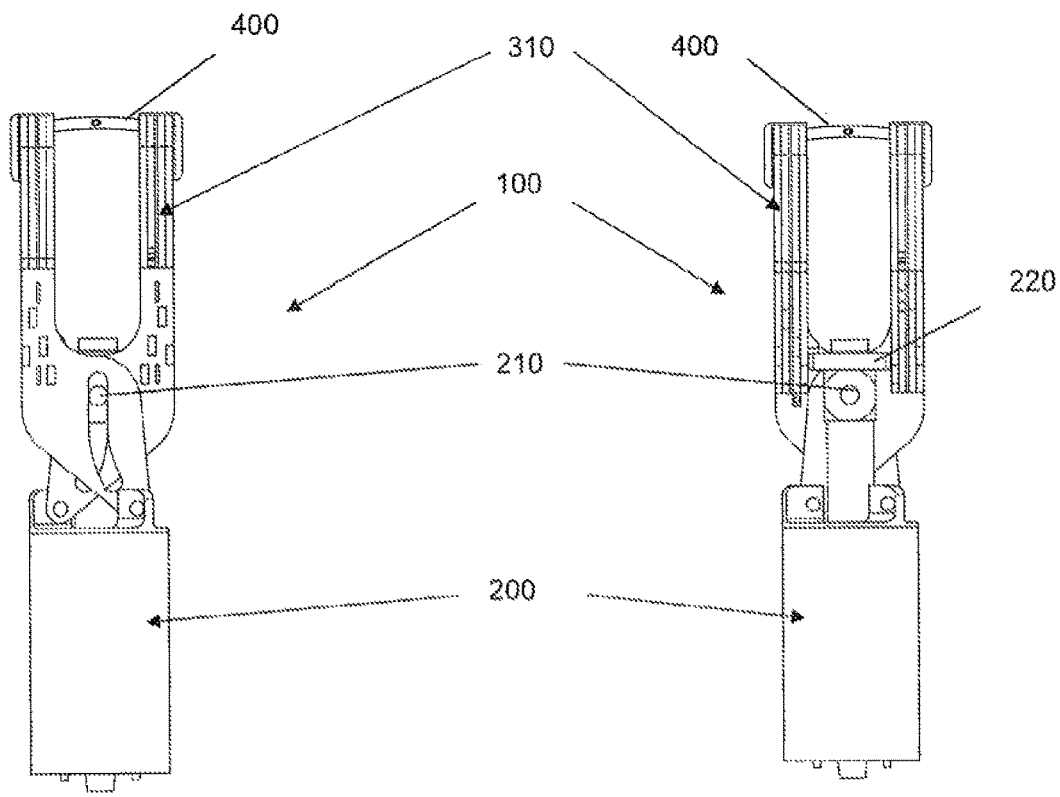
FIGS. 3A and 3B show two side views of the device of FIGS. 1A and 1B in a second closed position.

In FIG. 5, the end effector 100 according to the invention is shown in the position corresponding to the first closed position according to FIGS. 2A and 2B. The suture needle 400 is fixed here in the needle receptacle 340 of the first gripper jaw 310. The stop plate 220 is in direct contact with a pawl element 350, which can be displaced via a detent 351 using the stop plate 220 substantially along the longitudinal axis of the first jaw 310.

Figures 8A, 8B:
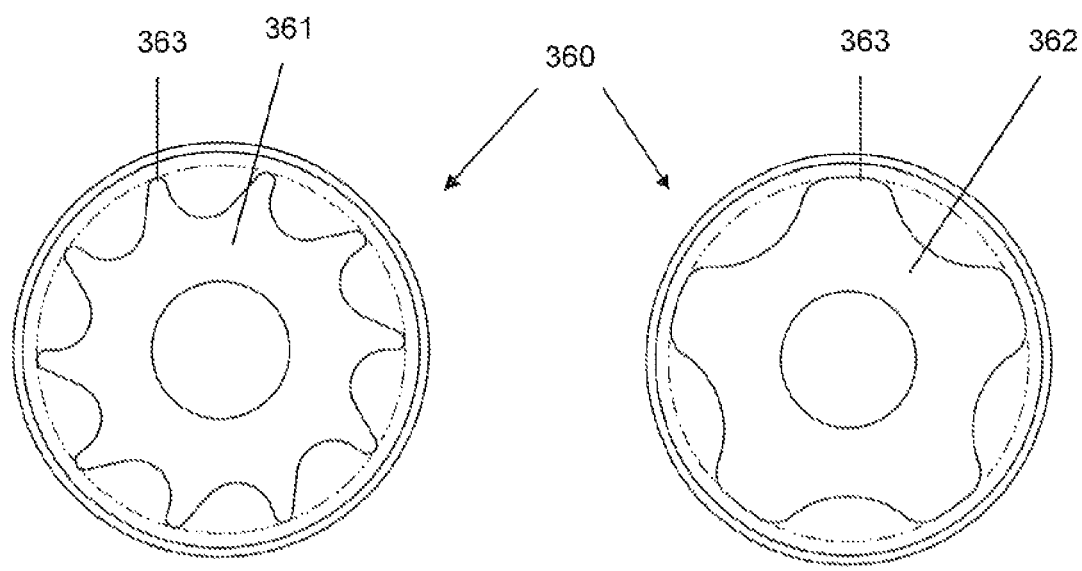
FIG. 8A shows a first side view of the gear element according to the invention.
FIG. 8B shows a second side view of the gear element according to the invention.

In this case, the pawl element 350 engages in a first gear 361 of a gear element 360, which is shown in detail in FIGS. 8A and 8B. The gear element 360 consists of two plane-parallel gears 361, 362, which have a different number of teeth 363. If the first gear 361 is now rotated, the second gear 362 also rotates due to the same axis of rotation. In the present example, the first gear 361 has ten teeth 363, while the second gear 362 of the gear element 360 has five teeth 363. Thus, this gear element 360 has a ratio of the actuation frequency of 1:2. In addition, the first gear 361 is designed as a ratchet wheel.

Figure 6A:
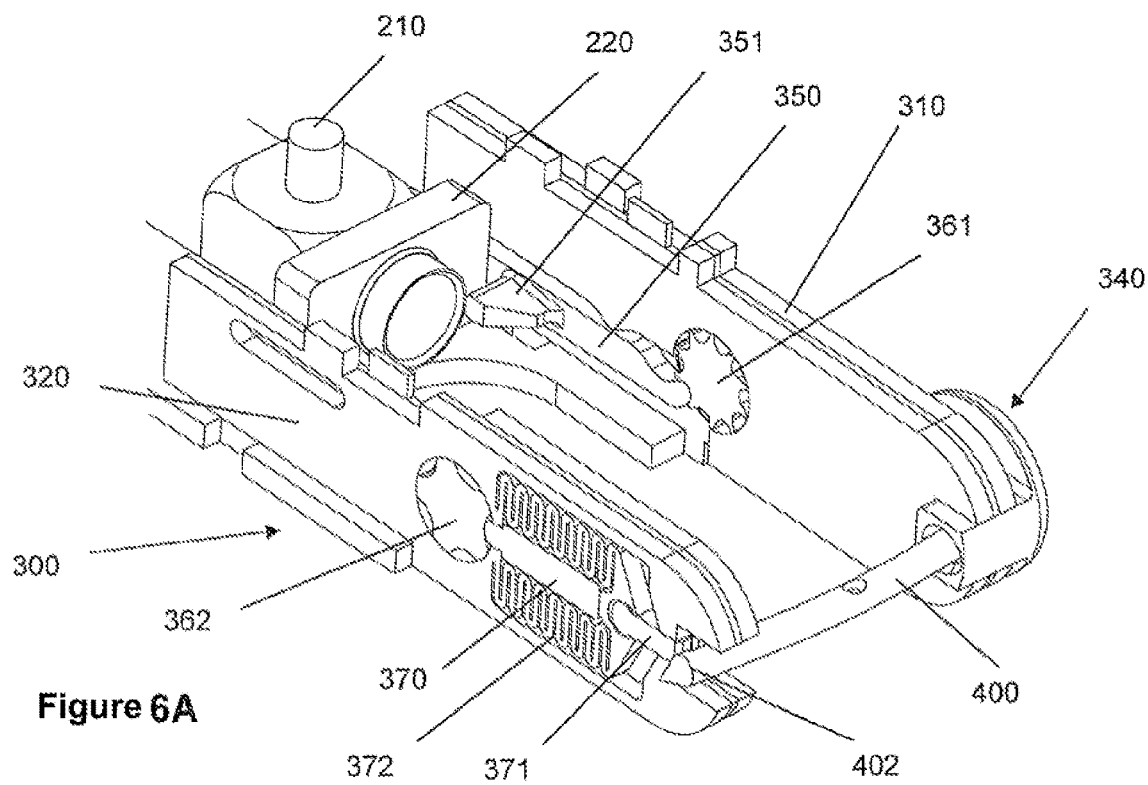
FIGS. 6A and 6B show the operating unit of the device of FIG. 5.
Figure 6B:
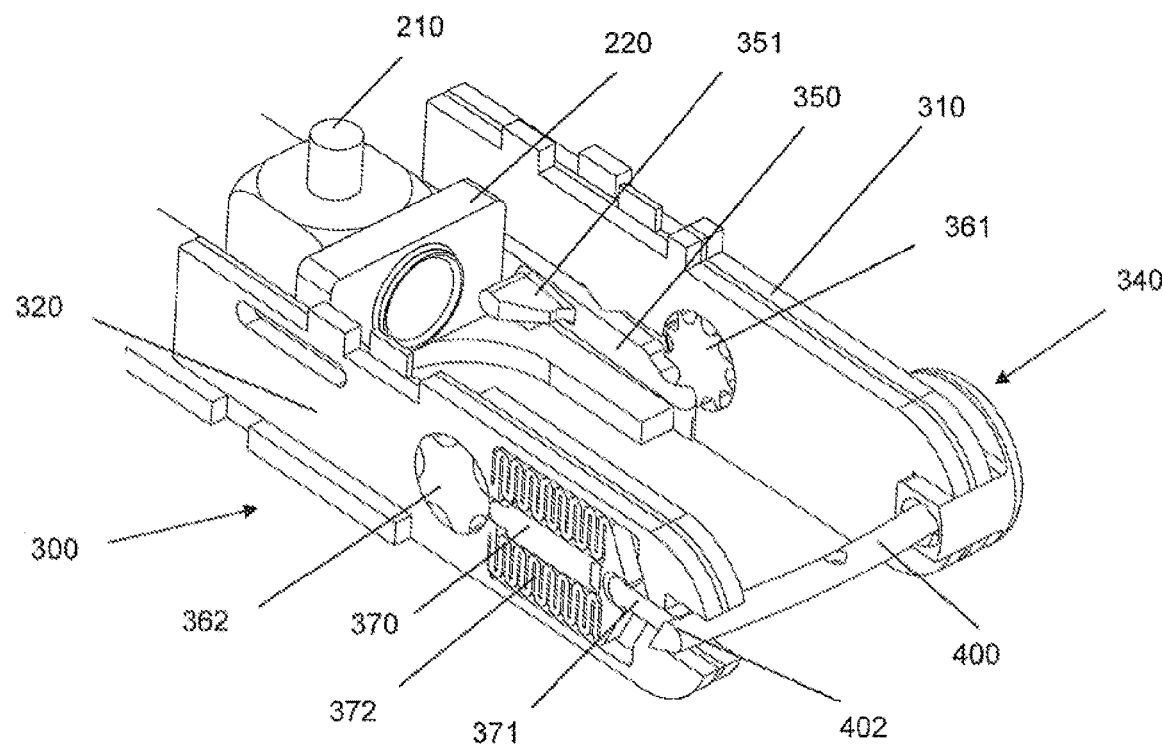
Figure 7:
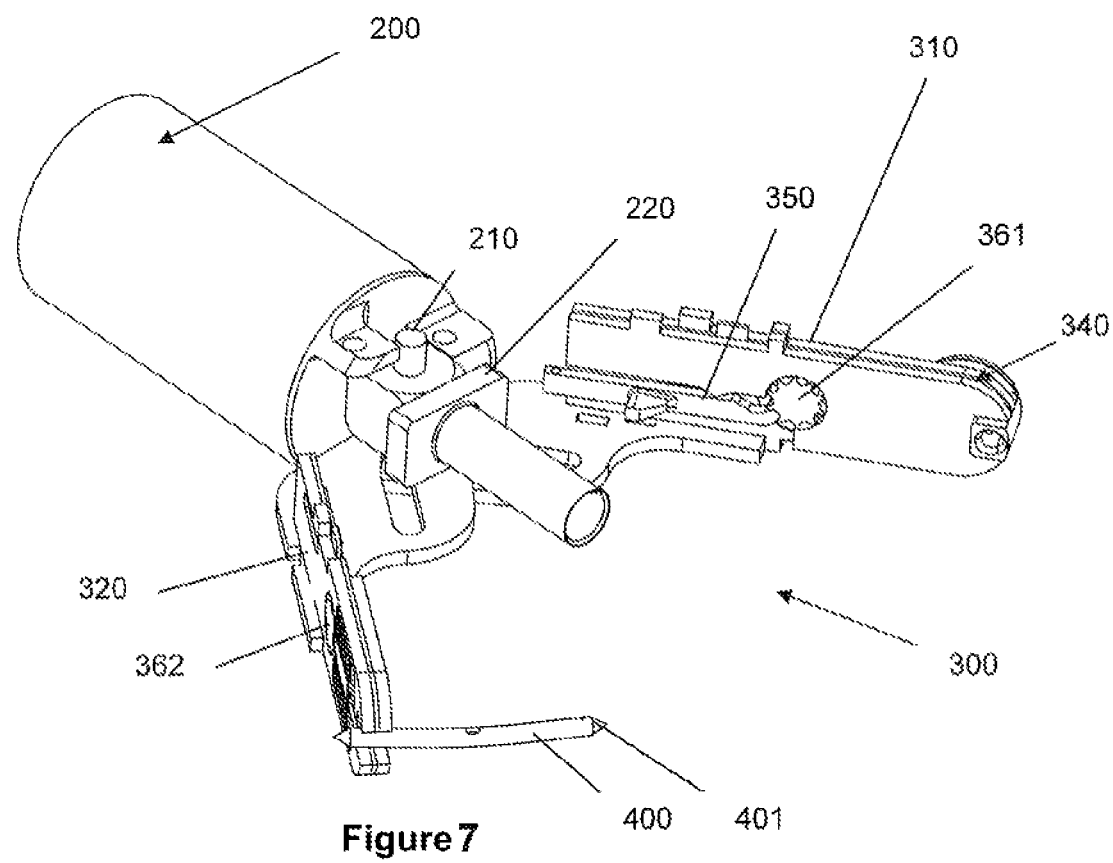
FIG. 7 shows the operating unit in the open state.

When the stop plate 210 is moved in the direction of the needle 400, the pawl element 350 is also moved in this direction, whereby the first gear 361 of the gear element 360 is rotated counterclockwise as shown in FIG. 6A. By rotating the first gear 361, the second gear 362 which is non-rotationally connected to the first gear 361 is rotated at the same time in the same direction, wherein due to the unequal number of teeth 363 of the first gear 361 and the second gear 362 a movement of a slide element 370 via the second gear 362 is triggered only with sufficient feed of the stop plate 210, which in turn produces a fixation or release of an end 401 of the suture needle 400.

The slide element 370 engages in the second gear 362, as shown in particular in FIG. 5 in the region of the second gripper jaw 320. This slide element 370 has at its end facing away from the second gear 362 a plunger 371, which is adapted to engage in the groove-like needle recess 410 of the suture needle 400, in order to fix the end 401, 402 of the suture needle 400 in the needle receptacle 340.

In FIG. 6A, the second end 402 of the suture needle 400 is still unfixed in the needle receptacle 340 of the second gripper jaw 320, wherein due to a further advancement of the sliding block 210 a rotation of the second gear 362 in the second jaw 320 causes the plunger 371 of the slide element 370 to be displaced in the second gripper jaw 320 such that it engages in the groove-like needle recess 410 of the suture needle 400, and thus fixes the second end 402 of the suture needle 400 in the needle receptacle 340.

Upon further advancement of the stop plate 210, the rotation of the gear element 360 of the first jaw 310 causes the plunger 371 to be retracted by means of a first spring element 372 and releases the first needle end 401 of the suture needle 400 in the needle receptacle 340 of the first gripper jaw 310.

If the end effector 100 is now opened again by moving the gripper jaws 310, 320 apart (FIG. 7), the suture needle 400 is now fixed in the second gripper jaw 320. By again closing the end effector 100 to the end position according to FIGS. 4A and 4B, the suture needle 400 is again arranged and fixed in the first gripper jaw 310. Thus, by alternately opening and closing the end effector 100, the needle 400 can be reciprocated between the two gripper jaws 310, 320 to thus perform a sewing motion to produce a surgical suture.

It is understood that the present invention is not limited to the illustrated embodiments. In particular, the shape of the gripper jaw and/or the suture needle can be designed differently, and it is not absolutely necessary that the movement of the jaw and/or the slide element and/or the pawl element is released by means of a hydraulic system. For example, in a further embodiment of the invention, the fixation or release of the respective ends 401, 402 of the suture needle 400 is further improved by providing additional spring elements for stabilizing the plunger 371. These additional spring elements provide a constant contact pressure of the plunger 371 in the groove-like needle recess 410. Further spring elements may further be provided for the stabilization and movement of the pawl element 350.

The invention claimed is:

1. A device for a medical instrument for applying a surgical suture, comprising:
    a release unit including a hydraulic system; and
    an operating unit including two pivotable gripper jaws, wherein each gripper jaw has a needle receptacle and a needle-fixing device;
    wherein the release unit is adapted for moving the two pivotable gripper jaws and additionally for actuating the needle-fixing device;
    wherein the needle-fixing device has at least one pawl element which is movable via the release unit, wherein the at least one pawl element cooperates with a gear element.

2. The device according to claim 1, wherein the gear element has two gears, which are arranged substantially plane-parallel to one another and have a different number of teeth.

3. The device according to claim 1, wherein the two gripper jaws each have a slot-like recess having a first end and a second end, in which a release element of the release unit is arranged.

4. The device according to claim 3, wherein the slot-like recess is a sliding block slide.

5. The device according to claim 1, wherein the needle-fixing device has at least one movable slide element, wherein the at least one moveable slide element is adapted to fix at least one suture needle in the needle receptacle.

6. The device according to claim 5, wherein the at least one moveable slide element cooperates with the gear element.

7. The device according to claim 5, wherein at least one first spring element cooperates with the at least one moveable slide element.

8. The device according to claim 7, wherein the at least one first spring element cooperates with the at least one pawl element.

9. A surgical instrument for applying a surgical suture, the surgical instrument comprising:
    an elongated element,
    an actuating device arranged at a proximal end of the elongated element, and
    a medical instrument arranged at a distal end of the elongated element and cooperates with the actuating device;
    wherein the medical instrument includes
        a release unit including a hydraulic system, and
        an operating unit including two pivotable gripper jaws, wherein each gripper jaw has a needle receptacle and a needle-fixing device,
        wherein the release unit is adapted for moving the two pivotable gripper jaws and additionally for actuating the needle-fixing device,
        wherein the needle-fixing device has at least one pawl element which is movable via the release unit, wherein the at least one pawl element cooperates with a gear element.

10. The surgical instrument according to claim 9, wherein the two gripper jaws of the operating unit are movable from an open position to a closed position, wherein in the open position a suture needle is fixed with its first needle end in the needle receptacle of a first gripper jaw of the two gripper jaws, and upon actuation of the release unit by the actuating device, a release element, in particular a sliding block slide, is movable along the slot-like recess, whereby the two gripper jaws can be transferred to the closed position, and at the same time a second needle end of the suture needle is fixable in the needle receptacle of a second gripper jaw of the two gripper jaws, while the first needle end of the suture needle is released in the needle receptacle of the first gripper jaw.

* * * * *